United States Patent [19]
Goldstein et al.

[11] Patent Number: 5,212,082
[45] Date of Patent: May 18, 1993

[54] GENETICALLY MODIFIED TYROSINE HYDROXYLASE AND USES THEREOF

[75] Inventors: Menek Goldstein; Jing Wu; David Filer; Arnold J. Friedhoff, all of New York, N.Y.

[73] Assignee: New York University, New York, N.Y.

[21] Appl. No.: 669,446

[22] Filed: Mar. 13, 1991

[51] Int. Cl.⁵ .................. C12N 9/04; C12N 15/00
[52] U.S. Cl. ........................... 435/190; 435/172.1; 935/14
[58] Field of Search ............... 435/190, 172.3; 935/14

[56] References Cited
PUBLICATIONS

Lee et al., *J. of Neurochem.* vol. 53, No. 4, 1989, pp. 1238–1244.
Campbell et al., *J. Biol. Chem.*, vol. 261, No. 23, Aug. 15, 1986, pp. 10489–10492.
Grime et al., *Nature*, vol. 326, Apr. 16, 1987, pp. 707–711.

Primary Examiner—Robert A. Wax
Assistant Examiner—Keith D. Hendricks
Attorney, Agent, or Firm—Browdy and Neimark

[57] ABSTRACT

Modification of the DNA encoding the enzyme tyrosine hydroxylase (TH) resulting in amino acid substitution in one of the first fifty five N-terminal residues, in particular replacing Ser-40 with Tyr or Leu, produced TH variants having substantially increased enzymatic activity upon transfection of suitable host cells. Cells transfected with the variant TH having enhanced enzymatic activity are useful for treating neurological or psychiatric disorders associated with deficient TH or dopamine, in particular Parkinson's disease, by grafting such cells into the brain.

5 Claims, 9 Drawing Sheets

FIG. 5A

```
human      10               20              30              40              50              60
      MPTPDDATTPQAKG FRRAVSE LDAKQAEAIMSPRFIGRRQSLIEDARKEREAAVAAAAAV
      ::::::         :::::::  ::::: ::::::  :::::::::::::::::    :
      MPTPSAPSPQPKG  FRRAVSEQDAKQAEAVTSPRFIGRRQSLIEDARKEREAAAAAAAV
rat        10              20              30              40              50              60

70              80              90             100             110             120
      PS -EPGDPLEAVAFEEKEGKAVLNLLFSPRATKPSALSRAVKVFETFEAKIHHLETRPAQR
      ::   :: :::::  :::  :: ::::::::  ::::: ::::::::::::::::::::::
      ASSEPGNPLEAVVFEERDGNAVLNLLFSLRGTKPSSLSRAVKVFETFEAKIHHLETRPAQR
              70              80              90             100             110             120

130             140             150             160             170             180
      PRAGGPHLEYFVRLEVRRGDLAALLSGVRQVSEDVRSPAGPKVPWFPRKVSELDKCHHLV
       :  :::::::::::  ::::::::: ::: :::::   :::::::::::::::::::::
      P LAGSPHLEYFVRFEVPSGDLAALLSSVRKVSDDVRSAREDKVPWFPRKVSELDKCHHLV
             130             140             150             160             170             180

190             200             210             220             230             240
      TKFDPDLDLDHPGFSDQVYRQRRKLIAEIAFQYRHGDPIPRVEYTAEEIATWKEVYTTLK
      ::::::::::::::::::::::::::::::::::  :: ::  ::::::::::::::::
      TKFDPDLDLDHPGFSDQVYRQRRKLIAEIAFQYKHGEPIPHVEYTAEEIATWKEVYVTLK
             190             200             210             220             230             240
```

FIG. 5B

```
            250        260        270        280        290        300
GLYATHACGEHLEAFALLERFSGYREDNIPQLEDVSRFLKERTGFQLRPVAGLLSAKDFL
::::::::::       ::   :::::       ::   :::::::::::::::::::::
GLYATHACREHLEGFQLLERYCGYREDSIPQLEDVSRFLKERTGFQLRPVAGLLSAKDFL
            250        260        270        280        290        300

310        320        330        340        350        360
ASLAFRVFQCTQYIRHASSPMHSPEPDCCHELLGHVPMLADRTFAQFSQDIGLASLGASD
::::::::::::::::::::::::::::::::::::::::::::::::::::::::::::
ASLAFRVFQCTQYIRHASSPMHSPEPDCCHELLGHVPMLADRTFAQFSQDIGLASLGASD
            310        320        330        340        350        360

370        380        390        400        410        420
EEIEKLSTLSWFTVEFGLCKQNGEVKAYGAGLLSSYGELLHCLSEEPEI RAFDPEAAAVQ
:::::::::: ::::::::::::::::::::::::::::::::::::::: ::::  :::
EEIEKLSTVYWFTVEFGLCKQNGELKAYGAGLLSSYGELLHSLSEEPEVRAFDPDT AAVQ
            370        380        390        400        410        420

430        440        450        460        470        480
PYQDQTYQSVYFVSESFSDAKDKLRSYASRIQRPFSVKFDPYTLAIDVLDSPQAVRRSLEGVQDELDTLAHALSAIG
::::::::: :::::::: :::::::: ::::::::::::::::::::::: :::   :::::::::  ::::::
PYQDQTYQPVYFVSESFNDAKDKLRNYASRIQRPFSVKFDPYTLAIDVLDSPHTIQ RSLEGVQDELHTLAHALSAIS
            430        440        450        460        470        480
```
490  497
490  498

FIG. 6A

```
                                Met Pro Thr Pro Asp Ala Thr Thr Pro Gln Ala Lys Gly Phe Arg
5' CCGACCTCCACACTGAGCCATGCCCACCCCGACGCCACCACGCCACAGGCCAAGGGCTTCCGC
           -10                1               10              20              30           40

Arg Ala Val Ser Glu Leu Asp Ala Lys Glu Ala Ile  Met Ser Pro Arg Phe Ile  Gly Arg Arg Gln
 AGGGCCGTGTCTGAGCTCGACGCTAAGGAGGCCATCATGTCCCCGCGGTTCATTGGGCGCAGGCAG
      50              60              70              80              90             100           110

Ser Leu Ile Glu Asp Ala Arg Lys Glu Arg  Glu Ala Val Ala  Ala Ala Ala Ala  Ala Val Pro Ser
 AGCCTCATCGAGGACGCCCGCAAGGAGCGGGAGGCGGTGGCAGCAGCCGCTCCAGTCCCCCTCG
      120             130             140             150             160             170           180

Glu Pro Gly Asp Pro Leu Glu  Ala Val Ala Phe Glu Glu Lys Glu  Gly Lys  Ala Val Leu Asn Leu Leu
 GAGCCCGGGGACCCCCTGGAGGCTGTGGCCTTTGAGGAGAAGGAGGGGAAGGCCGTGCTAAACCTGCTC
      190             200             210             220             230             240           250

PheSer Pro Arg  Ala Thr Lys Pro Ser Ala Leu Ser Arg Ala Val Lys Val Phe Glu Thr PheGlu Ala Lys
 TTCTCCCCGAGGGCCACCAAGCCCTCGGGCGCTGTCCCGAGCTGTGAAGGTGTTTGAGACGTTTGAAGCCAAA
      260             270             280             290             300             310           320
```

FIG. 6B

```
Ile His His Leu Glu Thr Arg Pro Ala Gln Arg Pro Arg Ala Gly Gly Pro His Leu Glu Tyr Phe Val Arg Leu
ATCCACCATCTAGAGACCCGGCCCCCAGAGAGGCCGCGAGCTGGGGGCCCCACCTGGAGTACTTCGTGCGCCT
330         340         350         360         370         380         390         400

Glu Val Arg Arg Gly Asp Leu Ala Ala Leu Leu Ser Gly Val Arg Gln Val Ser Glu Asp Val Arg Ser Pro
CGAGGTCCGCCGAGGGGACCTGGCCGCCCTGCTCAGTGGTGTGCGCCAGGTGTCAGAGGACGTGCGCAGCCC
        410         420         430         440         450         460         470

Ala Gly Pro Lys Val Pro Trp Phe Pro Arg Lys Val Ser Glu Leu Asp Lys Cys His His Leu Val Thr Lys
CGGGGGCCCCAAGGTCCCCTGGTTCCCCAAGAAAGTGTCAGACCTCGACAAGTGTCATCACCTGGTCACCAAG
480         490         500         510         520         530         540

Phe Asp Pro Asp Leu Asp His Pro Gly Phe Ser Asp Gln Val Tyr Arg Gln Arg Arg Lys Leu Ile Ala
TTCGACCCTGACCTGGACCACCCGGGCTTCTCGGACCAGGTGTACCCCAGCGCAGGAAGCTGATTGCT
550         560         570         580         590         600         610         620

Glu Ile Ala Phe Gln Tyr Arg His Gly Asp Pro Ile Pro Arg Val Glu Tyr Thr Ala Glu Ile Ala Thr
GAGATCGCCTTCCAGTACAGGCACGGCGACCCGATTCCCCGTGTGGAGTACACCGCCGAGGAGATTCCCACC
        630         640         650         660         670         680         690
```

FIG. 6C

Trp Lys Glu Val Tyr Thr Thr Leu Lys Gly Leu Tyr Ala Thr His Ala Cys Gly Glu His Leu Glu Ala Phe
TGGAAGGAGGTCTACACCACGCTGAAGGGCCTCTACGCCACGCACGCCTGCGGGGAGCACCTGGAGGCCTTT
700          710          720          730          740          750          760

Ala Leu Leu Glu Arg Phe Ser Gly Tyr Arg Glu Asp Asn Ile Pro Gln Leu Glu Asp Val Ser Arg Phe Leu
CCTTTGCTGGAGCGCTTCAGCGGCTACCGGGAAGACAATATCCCCCAGCTGGAGGAGGTCTCCCGCTTCCTG
770          780          790          800          810          820          830

Lys Glu Arg Thr Gly Phe Gln Leu Arg Pro Val Ala Gly Leu Leu Ser Ala Arg Asp Phe Leu Ala Ser
AAGGAGCGCACCAGGGGCTTCCAGCTGCGGCCTGTGGCCGGCCTGCTGTCCGCCCGGGACTTCCTGGCCAGC
840          850          860          870          880          890          900

Leu Ala Phe Arg Val Phe Gln Cys Thr Gln Tyr Ile Arg His His Ala Ser Ser Pro Met His Ser Pro Glu Pro
CTGGCCCTTCCGCGTGTTCCAGTGCACCCAGTATATCCGCCACCACGCTTCCTCTCCCATGCACTCCCCTGAGCCG
910          920          930          940          950          960          970

Asp Cys Cys His Glu Leu Leu Gly  His Val Pro Met Leu Ala Asp Arg Thr Phe Ala Gln Phe Ser Gln Asp Ile
GACTGCTGCCACGAGCTGCTGGGGCACGTGCCCATGCTGGCCGACCGCACCTTCGCGCAGTTCTCGCAGGACATT
980          990          1000         1010         1020         1030         1040         1050

Gly Leu Ala Ser Leu Gly Ala Ser Asp Glu Glu Lys Leu Ser Thr Leu Ser Trp Phe Thr Val Glu
GGCCTGGCGTCCCTGGGGGCCTCGGATGAGGAAAATTGAGAAGAGCTGTCCACGCTGTCATGGTTCACGGGTGGGAG
1060         1070         1080         1090         1100         1110         1120

FIG. 6D

```
Phe Gly Leu Cys Lys Gln Asn Gly Glu Val Lys Ala Tyr Gly Ala Gly Leu Leu Ser Ser Tyr Gly Glu Leu
TTCGGGCTGTGTGTAAGCAGAACGGGGAGGTGAAGCCCTATGGTGCCGGGCTGCTGTCCTCCTACGGGGAGCTC
     1130              1140              1150             1160              1170             1180              1190

Leu His Cys Leu Ser Glu Glu Pro Glu Ile Arg Ala Phe Asp Pro Glu Ala Ala Val Gln Pro Tyr Gln
CTGCACTGCCTGTCTGAGGAGCCCGAGATTCGGGCCTTCGACCCTGAGGCTGCGGCCGTGCAGCCCTACCAA
     1200              1210             1220             1230              1240             1250              1260

Asp Gln Thr Tyr Gln Ser Val Tyr Phe Val Ser Glu Ser Phe Ser Asp Ala Lys Asp Lys Leu Arg Ser Tyr
GACCAGACGTACCAGTCAGTCTACTTCGTGTCTGAGAGCTTCAGTGACGCCAAGGACAAGCTTCAGGAGCTAT
     1270              1280              1290             1300             1310              1320             1330              1340

Ala Ser Arg Ile Gln Arg Pro Phe Ser Val Lys Phe Asp Pro Tyr Thr Leu Ala Ile Asp Val Leu Asp Ser
CCCTCACGCATCCAGCGCCCCTTCTCCGTGAAGTTCGACCCGTACACGCTGGCCATCGACGTGCTGGACAGC
     1350              1360              1370             1380             1390             1400             1410

Pro Gln Ala Val Arg Arg Ser Leu Glu Gly Val Gln Asp Glu Leu Asp Thr Leu Ala His Ala Leu Ser Ala
CCCCAGGCCGTGCGGCGCTCCCTGGAGGGTGTCCACGATGAGCTGGACACCCTTGCCCATGCGCTGAGTGCC
     1420             1430             1440              1450             1460              1470             1480
```

FIG. 6E

```
Ile Gly STOP
ATTGGCTAGGTGCACGGGGTCCCTGAGGGCCCCTTCCCAACCTCCCCCTGGTCCTGCACTGTCCCGGAGCTC
     1490      1500      1510      1520      1530      1540      1550

AGGCCCCTGGTGAGGGGCTGGGTCCCGGGTGCCCCCATGCCCTCCCTGCTGCCAGGCTCCCACTGCCCCT
     1560      1570      1580      1590      1600      1610      1620

GCACCTGCTTCTCAGCGCAACAGTCTGTGTGCCCGTGGTGCTGCTGTGTGGTGAGGTCCTGT
     1630      1640      1650      1660      1670      1680      1690

CCTGGCTCCCAGGGTCCTGCTGGGGCTGCCACTGCCCCTTCCCGCCCCTGACACTGTCTCTGCTGCCCCAAT
     1700      1710      1720      1730      1740      1750      1760

CACCGTCACAATAAAAGAAACTGTGGTCTCTAAAAAAAAAAAA  3'
     1770      1780      1790      1800      1810
```

GENETICALLY MODIFIED TYROSINE HYDROXYLASE AND USES THEREOF

This invention was funded in part by research grants from the National Institute of Mental Health, No. MH 02717 and MH 35976, which provides to the United States Government certain rights in this invention.

BACKGROUND OF THE INVENTION

1. Field of the Invention

The invention in the fields of neuroscience and medicine relates to genetic modifications of the enzyme tyrosine hydroxylase resulting in genetic constructs encoding the variant enzyme having increased activity, which is useful in treating a variety of disorders associated with deficient tyrosine hydroxylase.

2. Description of the Background Art

The enzyme tyrosine hydroxylase (TH) catalyzes the rate-limiting step of catecholamine biosynthesis, the conversion of tyrosine to DOPA, the immediate precursor of dopamine (DA). TH utilizes tetra-hydropteridine as a cofactor in the enzymatic hydroxylation reaction. The activity of TH in the peripheral and central nervous system is subject to short and long term regulation by extra- and intracellular signals. Such signalling provides the mechanisms for modulation of the amount of DA (as well as norepinephrine and epinephrine) synthesized and available for secretion in response to physiological requirements.

Cyclic AMP (cAMP)-dependent phosphorylation of proteins plays a role in neuronal functions (Anagnoste, B. et al., *J. Pharmacol. Exp. Ther.* 101:370-376 (1974); Ebstgein, B. et al., *J. Pharm. Pharmacol.* 26:975-977 (1974); Goldstein, M. et al., *Brain Res.* 109:563-574(1976)). Cyclic AMP-dependent protein kinase (protein kinase A or PKA) phosphorylates and activates TH in vitro (Joh, T. H. et al., *Proc. Natl. Acad. Sci. USA* 75:4744-4748 (1978); Markey, K. A. et al.. *Mol. Pharmacol.* 17:79-85 (1979); Morgenroth, V. H., III. et al., *J. Biol. Chem.* 250:1946-1948 (1975)). Activation of TH by nerve stimulation produces changes in its kinetic constants similar to those produced in vitro following phosphorylation by PKA (Vulliet, P. R. et al.. *Proc. Natl. Acad. Sci. USA* 77:92-96 (1980)).

A number of extracellular signals produce activation and phosphorylation of TH using at least three different protein kinases: PKA, calmodulin-dependent multiple protein kinase (CaM-dependent PKII) (Vuillet et al.. supra; Yamauchi, T. et al.. *Biochem. Biophys. Res. Comm.* 100:807-813 (1981)), and $Ca^{2+}$-phospholipid-dependent protein kinase C (PKC) (Albert, K. A., *Proc. Natl. Acad. Sci. USA* 81:7713-7717 (1984); Raese, J. D. et al., *Commun. Psychopharmacol.* 3:295-301 (1979); for review, see: Goldstein, M. et al., *Psychopharmacology: The Third Generation of Progress*, Meltzer, H. Y., ed., Raven Press, New York, 1987, which reference is hereby incorporated by reference). Phosphorylation of TH by PKA correlates with increased TH catalytic activity (Goldstein et al., 1976, supra, Joh et al.. supra: Morgenroth et al., supra; Meligeni, J. A. et al., *J. Biol. Chem.* 257:12642-12640 (1982)). In purified TH preparations from cultured PC12 cells, an adrenal chromaffin cell line, purified exogenous kinase A increased $^{32}P$ incorporation from gamma[$^{32}P$]ATP, and the radioactivity was associated with the 62 kDa subunit of the TH enzyme (Goldstein, M. et al., *J. Pharm. Pharmacol.* 22:715-716 (1970); Haycock, J. W. et al., *J. Biol. Chem.* 257:12641-12648 (1982)).

The activation of TH by CaM-dependent PKII requires the presence of an activating protein, and the phosphorylated enzyme shows a pH profile similar to that of the nonphosphorylated enzyme. In contrast to this kinase, CaM-dependent protein kinase I does not appear to phosphorylate or activate TH. TH phosphorylated by PKC has kinetic properties similar to those of TH phosphorylated by PKA. Thus, TH phosphorylated by PKA or PKC has a higher affinity for pteridine cofactor and lower affinities for catechol end-products. The kinetic changes suggest that phosphorylation of TH by PKA and PKC is involved in the control of TH activity in physiological and pathological states, and that the non-phosphorylated TH may represent an inactive or less active reservoir. The finding that phosphorylation-dephosphorylation of TH is reversible and is associated with activation and deactivation of the enzyme also supports the notion that these mechanisms have a regulatory function in the synthesis of catecholamines.

When phosphorylation is catalyzed by PKA or PKC, a single major phosphorylated peptide species is generated by tryptic-chymotryptic digestion of TH. Phosphorylation by CaM-dependent PKII results in two phosphopeptides. Nerve growth factor (NGF) treatment of PC12 cells also enhances phosphorylation, though apparently mediated by a distinct kinase that results in a single tryptic-chymotryptic phosphopeptide. The relevance of phosphorylation at each site to the activity of TH is not yet known.

Acute administration of neuroleptic drugs increases the firing rate of DA neurons and increases turnover and synthesis of DA. This is thought to be due to TH phosphorylation by a cAMP-independent protein kinase. The deactivation of TH following long-term treatment of rats with neuroleptics may result from dephosphorylation (Lerner, P. et al., *Science* 197:181-183 (1977)). TH activated by haloperidol has been said to represent a mixture of phosphorylated and nonphosphorylated forms of the enzyme.

In summary, at least three distinct classes of well-characterized protein kinases have been found to catalyze the phosphorylation of a large number of neuronal proteins. Interestingly, TH is a substrate for all three of these kinases, and perhaps for others as well. It is not clear whether this represents a biological redundancy, or whether phosphorylation in vivo with two or more kinases can result in additive, nonadditive, synergistic or antagonistic effects.

K. Y. Lee et al. (*J. Neurochem.* 53:1238-1244 (1989)) discovered that a peptide corresponding to position 32-47 in rat TH (termed TH-16) induced rabbit polyclonal antibodies which could modulate TH enzymatic activity. Such antibodies (termed anti-TH-16) enhanced the enzymatic activity in a concentration-dependent manner. This antibody did not appear to inhibit phosphorylation of the enzyme at Ser-40. Lee et al. also referred to studies showing that TH was activated by limited trypsin or chymotrypsin proteolysis (Petrack, B. et al.. *J. Biol. Chem.* 243:743-748 (1968); Shiman, R. et al., *J. Biol. Chem.* 246:1330-1340 (1971)), presumably involving the N-terminus. The Lee et al. reference further suggests that antibody-induced activation may result from stabilization of a conformational state in the vicinity of Ser-40, or that a conformational change induced by the antibody facilitates phosphorylation.

The suggestion was made that the antibody produces a conformational change near the Ser-40 phosphorylation site similar to that produced by phosphorylation with PKA or PKC.

The gene for human TH has been cloned and sequenced. Four similar but distinct mRNAs, produced through alternative splicing from a single gene result in different TH "isozymes." For a description of the structure of the human TH gene, see: Grima, B. et al., *Nature* 326:707-711; Le Bourdelles, B. et al., *J. Neurochem.* 50:988-991 (1988); Horellou, P. et al.. *J. Neurochem.* 51:652-655 (1988); Kobayashi, et al., *J. Biochem.* 103:907-912 (1988); Nagatsu, T., *Cell. Mol. Neurobiol.* 9:313 (1989), which references are hereby incorporated by reference).

Parkinson's disease (PD) results from a selective loss of DA-releasing (dopaminergic) nigrostriatal neurons. This causes a loss of neural input from the substantia nigra to the striatum. Classically, PD has been treated by supplying L-DOPA which acts as a compensatory source of DA. However, this mode of therapy is accompanied by a number of undesired side effects (Adams, R. D. et al.. *Principles of Neurology*. 4th Edition, McGraw-Hill, New York, 1989)). Alternative approaches to pharmacotherapy involving the grafting of cells into the brain, have been considered and tested during recent years.

Solid grafts of tissues potentially capable of producing DA, such as adult adrenal medulla and embryonic substantia nigra (SN), have been used extensively for experimental grafting in rats and primates treated with 6-hydroxydopamine (6-OHDA) to destroy dopaminergic cells (Dunnett, S. B. et al., *Brain Res.* 215: 147-161 (1981); Dunnett, S. B. et al.. *Brain Res.* 229:457-470 (1981); Morisha, J. M. et al., *Exp. Neurol.* 84:643-654 (1984); Perlow, M. J. et al., *Science* 204:643-647 (1979)). Grafts of embryonic SN tissue have also been used to treat primates lesioned with the neurotoxin 1-methyl-4-phenyl-1,2,3,4-tetrahydropyridine (MPTP), which produces a PD-like syndrome (Redmond, D. E. et al., *Lancet* 8490:1125-27 (1986)).

Stenevi et al. (*Brain Res.* 114:1-20 (1976)) reported that optimal engraftment occurred when (a) fetal CNS neurons were used, and (b) the transplanted cells were placed next to a rich vascular supply. A review of the literature reveals that tissue from almost every area of the fetal brain can be successfully transplanted if care is taken with procedural details (see, for example, Olson, L. A. et al.. In: *Neural Transolants: Development and Function*, Sladek, J. R. et al.. eds, Plenum Press, New York, 1984, pp. 125-165). Embryonic tissue provides a good source of cells which will differentiate in a foreign environment and become integrated with the host tissue (Dunnett et al., Morisha et al., Perlow et al.. supra; Wuerthele, S. M. et al., In: *Catecholamines, Part B*, E. Usdin et al., eds., A. R. Liss, Inc., New York, pp. 333-341).

In contrast to successful grafting of fetal neural tissue, mature CNS neurons have never been found to survive in transplants (Stenevi, U. et al.. *Brain Res.* 114:1-20 (1976)). Among other reasons, this advantage of fetal tissue may be due to its responsiveness to growth (or "survival") factors present in the milieu of the damaged host brain (Nieto-Sampedro, M. et al., *Science* 217:860-861 (1982); Nieto-Sampedro, M. et al., *Proc. Natl. Acad. Sci. USA* 81:6250-6254 (1984)). However, despite the promise of fetal tissue and cell transplants, the art has turned to alternate sources of donor tissues for transplantation because of the ethical, moral, and legal problems attendant to utilizing fetal tissue in human medicine.

Thus, the feasibility of the transplant approach has been established experimentally. However, this approach is severely limited by the dependence on fetal tissue, which is of limited availability and great political controversy. In essence, transplantation of human fetal tissue from aborted pregnancies has been prohibited in the United States.

Potential sources of donor tissue for neural implants include neural and paraneural cells from organ donors and cultured cell lines. (See, for example: Gash, D. M. et al., In: *Neural Graftino in the Mammalian CNS*, Bjorklund, A. et al., eds, Elsevier, Amsterdam, 1985, pp. 595-603; Gash, D. M. et al.. *Science* 233:1420-22 (1986)). Adrenal medullary cells are derived from the neural crest and, like sympathetic neurons, grow processes in vivo or in vitro in response to nerve growth factor (NGF) (Unsicker, K. et al.. *Proc. Natl. Acad. Sci. USA* 75:34983502 (1978)) and can survive in the brain of 6-OHDA treated rats for at least 5 months, and produce DA (Dunnett et al.. supra; Freed, W. J. et al., *Ann. Neurol.* 8:510-519 (1980); Freed, W. J. et al. *Science* 222:937-939 (1983)).

Thus, a great need exists for new approaches to provide cells to the central nervous system which can supplement or replace missing factors, such as synthetic enzymes or growth factors, in a variety of debilitating neurological or psychiatric disease. It is to this end that the present invention is directed.

SUMMARY OF THE INVENTION

Based on earlier studies in their laboratory of activation of tyrosine hydroxylase (TH) enzymatic activity by phosphorylation and with antibodies (Lee, K.Y. et al., supra), the present inventors have conceived of a novel way to enhance substantially the activity of TH by inducing substitutions at particular amino acid residues in the N-terminal portion of the molecule using molecular genetic techniques. As a result of these modifications, they have obtained genetic constructs which encode variant TH enzymes. Upon transfection of host cells with these genetic constructs, the cells express the variant TH, and manifest higher TH activity compared to cells transfected by constructs containing the wild-type TH.

These genetic constructs, and cells transfected thereby, are useful in treating a number of diseases or conditions associated with defective function of the TH enzyme. Such diseases include Parkinson's disease, affective disorders, and Alzheimer's disease.

The mechanism of increased TH enzyme activity may be related to altered phosphorylation or mainly to conformational changes in the enzyme. Certain mutations in the N-terminal region, in particular in the first fifty five residues, which is distal from the active site, result in increased enzymatic activity. Regardless of mechanism responsible, the present inventors have discovered, and provide herein, new and useful DNA and protein variants of TH.

Thus, the present invention is directed to a variant tyrosine hydroxylase protein molecule having at least one amino acid substitution in the N-terminal fifty five amino acid residues of the wild-type protein sequence, where this substitution is either at a potential phosphorylation site, or at any position between amino acid 37 and 47, wherein the enzymatic activity of the variant protein is substantially greater than the enzymatic activity of the wild-type protein, preferably at least about three times greater.

Preferably, the TH protein has an amino acid substitutions at Ser-8, Ser-19, Ser-31, Arg-38, Ser-40, Glu-43 or Arg-46 in rat TH (see FIG. 5), or a substitution at an equivalent site in TH of another animal species. A most preferred substitution is Ser-40 to Tyr or Leu.

In the human TH protein (see FIG. 5) similar substitutions are preferred at homologous residues in the N-terminal region. The preferred sites for amino acid substitutions include Ser-19, Ser-31, Arg-37, Arg-38, Ser-40, Leu-41, Ile-42, Glu-43, Asp-44, Ala-45, Arg-46 or Lys-47. Most preferred substitutions are Ser-40 to Tyr or Leu.

In another embodiment, the present invention is directed to a DNA molecule encoding a variant tyrosine hydroxylase protein, rat or human, as described above. Preferably, the DNA is a cDNA. In one embodiment, the DNA molecule of the present invention is an expression vehicle, preferably a plasmid.

The present invention also includes a host cell transfected with the DNA molecule described above, wherein the host cell expresses the tyrosine hydroxylase enzyme. Eukaryotic hosts, in particular mammalian cells, especially human cells, are preferred.

The present invention also includes a process for preparing a variant tyrosine hydroxylase protein as above, comprising:

(a) culturing a host capable of expressing the protein under culturing conditions,
(b) expressing the protein; and
(c) recovering the protein from the culture.

The present invention also provides an antibody specific for the variant rat or human TH protein, preferably a monoclonal antibody, which has substantially no cross-reactivity with the native TH.

The present invention is further directed to a method for treating a neurological or psychiatric disease associated with a deficiency in tyrosine hydroxylase or of DA in a subject, comprising grafting into the brain of the subject an effective number of human host cells expressing the variant TH enzyme, preferably the variant human TH enzyme. This method can be used for Parkinson's disease, Alzheimer's disease, or an affective disorder. A preferred embodiment is the treatment of Parkinson's disease according to the above method.

BRIEF DESCRIPTION OF THE DRAWINGS

FIG. 5a–5b show the amino acid sequences of human and rat TH, in alignment. The homology is about 84.2% in the N-terminus, from amino acids 1-190, and about 91.5% in the C-terminal domain. Asterisks identify phosphorylation sites experimentally demonstrated in rat TH and their human homologues.

FIG. 6a–6e shows the nucleotide sequence and derived amino acid sequences of cDNA clones for human TH. The putative polyadenylation site is underlined.

DESCRIPTION OF THE PREFERRED EMBODIMENTS

Figure 1:
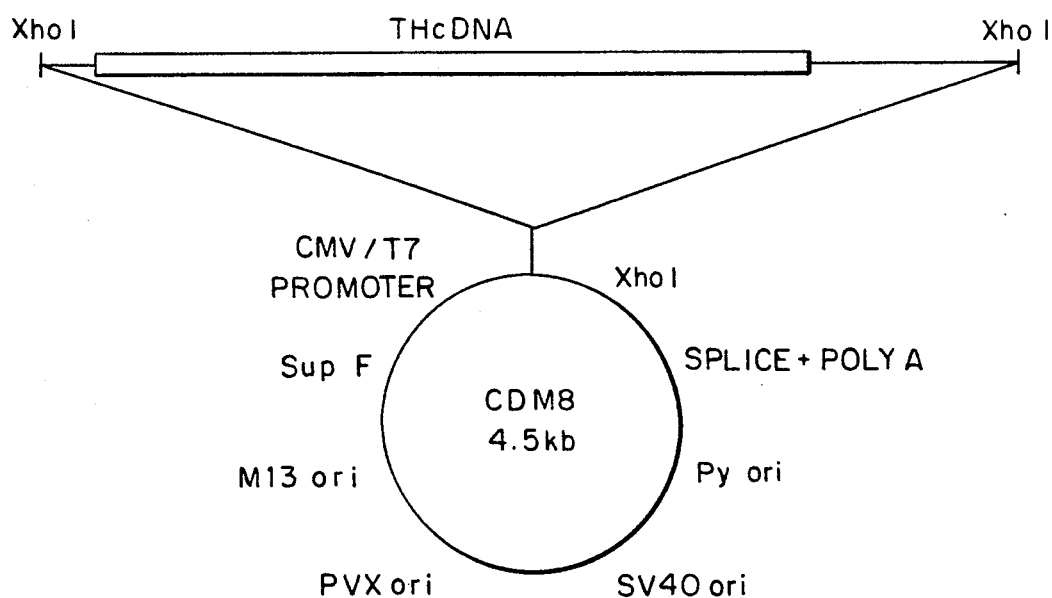
FIG. 1 shows a map of the rat TH gene in the expression vector CDM8TH. The construct contains human cytomegalovirus AD169 IE promoter and T7 promoter. The splice and poly A addition site signals are located downstream of the gene insert. SupF: sYnthetic tYrosine suppressor tRNA gene; M13 ori: M13 origin; PVX ori: PiVX origin; SV40 ori: SV40 origin (enhancer-less); Py ori: Polyoma origin and enhancers.

The present invention is directed to an amino acid substitution variant of the tyrosine hydroxylase (TH) enzyme having substantially enhanced enzymatic activity compared to the wild-type enzyme, DNA encoding the variant TH, hosts expressing the variant TH, and methods of using the DNA and hosts to treat a subject having a disease or condition associated with decreased or abnormal TH activity.

The present inventors have found that substitution of Tyr or Leu for Ser-40 in rat TH results in a tripling of enzymatic activity. In light of these results and the earlier observations of K. Y. Lee et al., supra, the present inventors appreciated the importance of the protein structure, and/or capacity for phosphorylation, particularly in the environment of the Ser-40 residue, for enzyme activity. The scope of the present invention resulted from appreciation of the notion that amino acid substitutions of either of two categories could be used to enhance TH enzyme activity. First, based on the fact that substitution for Ser-40 with either Tyr or Leu, but not with Cys, enhanced enzyme activity, the significance of removing a potential phosphorylation site in the N-terminal region was discovered. Second, based on the results of substituting at Ser-40, and the effects of an antibody for a peptide having the sequence of that region (Lee, K. Y., et al.), the significance of modifying any of a number of sites in the 37-47 region, the area surrounding Ser-40, was appreciated. While it is possible that changes elsewhere in the molecule may also result in similar enhancement of activity, the dramatic results reported herein with respect to substituting Tyr or Leu for Ser-40 reinforce the notion of the particular importance of this region, and phosphorylation sites in particular.

The lack of enhanced activity by substituting Cys for Ser-40 indicates that not all substitutions will work. Cys is a relatively small amino acid, similar in size to Ser. Since Tyr is a larger amino acid, containing an aromatic ring, it is particularly predicted that any of the larger amino acids, such as Phe and Trp, can be used in place of Tyr to achieve similar results. Because Leu is a relative large amino acid with a non-polar side chain, it is further predicted that any similar amino acid such as Ile and Val in place of Leu will also achieve similar results. Based on this teaching, one of ordinary skill in the art will know how to select sites and particular amino acid substitutions to achieve enhanced TH activity for the enzyme from any species given the amino acid sequence of the N-terminal region.

Since perturbation of the conformation in the regions appears to be a likely basis for the enhanced enzymatic activity, replacing a larger amino acid with a smaller one or one of substantially different electrochemical properties (e.g. hydrophilic vs. hydrophobic side chain) also would be predicted to induce enhanced activity, for example, replacement of Leu-41 or Ile-42 in human TH with Gly, Met or Cys.

Based on the foregoing, the preferred "variant" of the wild-type TH, according to the present invention, is one wherein a single amino acid has been substituted in the N-terminal 55 amino acid residues of the protein in order to produce substantially increased enzymatic activity. More than one substitution is possible provided that the variant protein has substantially increased enzymatic activity. A most preferred substitution in rat TH is at position Ser-8, Ser-19, Ser-31, Arg-38, Ser-40, Glu-43 or Arg-46. In particular, substitution of Tyr or Leu for Ser-40 is preferred.

Preferred variants of wild-type human TH have amino acid substitution at Ser-19, Ser-31, Arg-37, Arg-38, Ser-40, Leu-41, Ile-42, Glu-43, Asp-44, Ala-45, Arg-46 or Lys-47, as shown in FIG. 5. The preferred substitution is Tyr or Leu for Ser-40.

Other variants within the scope of the present invention include substitutions of more than one amino acid residue, provided that the final construct possesses TH enzymatic activity which is substantially increased, preferably by at least about three-fold, compared to wild-type TH. One of ordinary skill in the art can readily determine this increased activity, without undue experimentation, using standard radioenzymatic or other enzymatic assays for TH well-known in the art.

While the present invention comprehends variants which include many possible permutations and combinations of the amino acid sequence of wild-type TH, it is limited to those which provide substantially greater enzymatic activity than that of the wild-type. There is good reason to believe, based on the discoveries disclosed herein, that a great many of the proposed substitutions will have the desired effect. The present specification teaches how to achieve desired mutations and how to test any given TH variant to determine whether its enzymatic activity is substantially greater than that of the wild-type. While substantial work may be involved, the type of experimentation is not undue, and is routine for those of ordinary skill in this art.

Because of the known activity-enhancing effect of certain substitutions at Ser-40 and of antibodies specific to the protein in the region of Ser-40, it is reasonable to predict that many other substitutions in this area will result in a similar effect. Because of the known effect of removing the phosphorylation site at Ser-40, it is reasonable to predict that substitutions at other phosphorylation sites in the N-terminal domain would also result in a similar effect. Thus, there is a reasonable expectation of success and confirming experimentation to specifically identify other TH variants with the desired activity is not undue.

Amino acid sequence variants of TH can be prepared by mutations in the DNA which encodes TH. Obviously, the mutations that will be made in the DNA encoding the variant peptide must not alter the reading frame and preferably will not create complementary regions that could produce secondary mRNA structure (see European Patent Publication No. EP 75,444).

Preferred mutations resulting in variant TH molecules with amino acid substitutions have been described above. The PCR primers used to obtain the DNA having some of the substitutions for rat TH are summarized in Table 1, below. Appropriate PCR primers for use with human TH DNA (see FIG. 6) will hybridize with sites homologous to those shown for rat TH DNA in Table 1. One of ordinary skill in the art will know how to design, produce and use such primers from examination of the sequence of the human TH gene without undue experimentation, given the teachings of the present invention.

A "fragment" of the variant TH refers to any subset of the molecule, that is, a shorter peptide.

A "chemical derivative" of the variant TH contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues. For example, derivatization with bifunctional agents, well-known in the art, is useful for cross-linking the protein or peptide to a water-insoluble support matrix or to other macromolecular carriers.

As used herein, the term "variant TH enzyme or protein" is intended to include a fragment or chemical derivative of the enzyme, providing that the fragment or chemical derivative has increased TH enzymatic activity, as described herein. Such a variant TH enzyme is useful in the acute treatment of a syndrome of DA insufficiency, such as in hypertensive crisis or cardiac insufficiency. The enzyme may be administered directly or in encapsulated form for controlled release, for example using biocompatible polymer capsules and other materials well-known in the art (see, for example, Aebischer, P. et al., U.S. Pat. 4,892,538; Aebischer, P. et al., *Brain Res.* 448:364–368 (1988); Winn, S. R. et al., *J. Biomed Mater Res.* 23:31–44 (1989)). Alternatively, the variant enzyme molecule, fragment or derivative of the present invention may be used in an immunoassay, together with an antibody of the present invention (see below) to monitor the enzyme during one of the treatment regimens performed according to the present invention.

The derivatized moieties may improve the solubility, absorption, biological half life, and the like of the enzyme. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980).

Standard reference works setting forth the general principles of recombinant DNA technology and cell biology, which are hereby incorporated by reference, include Watson, J. D., et al., *Molecular Biology of the Gene*, Volumes I and II, Benjamin/Cummings Publishing Co., Inc., Menlo Park, Calif. (1987); Darnell, J. E. et al., *Molecular Cell Biology*, Scientific American Books, Inc., New York, N.Y. (1986); Lewin, B. M., *Genes II*, John Wiley & Sons, New York, N.Y. (1985); Old, R. W. et al., *Principles of Gene Manipulation: An Introduction to Genetic Engineering*, 2nd Ed., University of California Press, Berkeley, Calif. (1981); Maniatis, T., et al. (*Molec-* ular Cloning: A Laboratory Manual, Cold Spring Harbor Press, Cold Spring Harbor, N.Y. (1982)); Sambrook, J. et al. (Molecular Cloning: A Laboratory Manual, 2nd Edition, Cold Spring Harbor Press, Cold Spring Harbor, N.Y. (1989) and Albers, B. et al.. Molecular Biology of the Cell, 2nd Ed., Garland Publishing, Inc., New York, N.Y. (1989).

At the genetic level, the TH variants of the present invention ordinarily are prepared by site-directed mutagenesis (see, generally, Adelman et al., DNA 2:183 (1983)) of nucleotides in the DNA encoding the peptide molecule, preferably using the PCR methods described below. A preferred method for site-directed mutagenesis is described by Horton et al. (Horton, R. M. et al.. Biotechniques 8:528–535 (1990), hereby incorporated by reference). Preferred PCR primers to achieve the desired amino acid substitutions in rat TH are shown in Table 1. The DNA encoding variant TH proteins is subsequently introduced into cells which express the variant TH protein having increased enzyme activity.

TABLE 1

Site-Directed Mutagenesis of Tyrosine Hydroxylase

| AMINO ACID Native→Substitute | Wild-type or Mutant | Primer |
| --- | --- | --- |
| Ser-40 Tyr | (WT) | CGGCCGAGAGTTCTTCATTCGAG |
|  | (M) | CGGCCGACCAGTATCTCATCGAG |
| Arg-38 Leu | (WT) | ATCGGACGGCGACAGTCT |
|  | (M) | ATCGGACGGCTACAGAGTCT |
| Arg-46 Cys | (WT) | GAGCATGCCCGCAAGGA |
|  | (M) | GAGCATGCCTGCAAGGA |
| Glu-43 Ala | (WT) | AGTCTCATCGAGGATGCC |
|  | (M) | AGTCTCATCGCGGATGCC |

In addition to site-directed mutagenesis, variant TH genes may be created using homologous recombination. Homologous recombination is a technique developed within the past few years for targeting genes to induce or correct mutations in transcriptionally active genes (Kucherlapati, Prog. Nucl. Acid Res. Mol. Biol. 36:301 (1989)) and permits introduction of specific mutations into specific regions of the mammalian genome (Thomas et al., Cell 44:419–428 (1986); Thomas et al., Cell 51:503–512 (1987); Doetschman et al., Proc. Natl. Acad. Sci. USA 85:8583–8587 (1988)). Through this technique, a segment of DNA to be inserted into the genome can be directed to a specific region of the gene of interest by attaching it to "targeting DNA". "Targeting DNA" is DNA that is complementary (homologous) to a region of the genomic DNA. If two homologous pieces of single stranded DNA (i.e., the targeting DNA and the genomic DNA) are in close proximity, they will hybridize to form a double stranded helix. Attached to the targeting DNA is the DNA sequence that one desires to insert into the genome.

There are a number of methods by which homologous recombination can occur. One example is during the process of replication of DNA during mitosis in cells.

Through a mechanism that is not completely understood, parental double-stranded DNA is opened immediately prior to cell division at a local region called the replication bubble. The two separated strands of DNA may now serve as templates from which new strands of DNA are synthesized. One arm of the replication fork has the DNA code in the 5' to 3' direction, which is the appropriate orientation from which the enzyme DNA polymerase can "read". This enzyme attaches to the 5' portion of the single stranded DNA and using the strand as a template, begins to synthesize the complementary DNA strand. The other parental strand of DNA is encoded in the 3' to 5' direction. It cannot be read in this direction by DNA polymerase. For this strand of DNA to replicate, a special mechanism must occur.

A specialized enzyme, RNA primase, attaches itself to the 3' to 5' strand of DNA and synthesizes a short RNA primer at intervals along the strand. Using these RNA segments as primers, the DNA polymerase now attaches to the primed DNA and synthesizes a complementary piece of DNA in the 5' to 3' direction. These pieces of newly synthesized DNA are called Okazaki fragments. The RNA primers that were responsible for starting the entire reaction are removed by the exonuclease function of the DNA polymerase and replaced with DNA. This phenomenon continues until the polymerase reaches an unprimed stretch of DNA, where the local synthetic process stops. Thus, although the complementary parental strand is synthesized overall in the 3' to 5' direction, it is actually produced by "backstitching" in the 5' to 3' direction. Any nicks that might occur in the DNA during the "backstitching" process are sealed by DNA ligase.

To maintain an absolute fidelity of the DNA code, a proofreading function is present within the DNA polymerase. The DNA polymerase requires primed pieces of DNA upon which to synthesize a new strand of DNA. As mentioned above, this can be a single strand of DNA primed with RNA, or a complementary strand of DNA. When the DNA polymerase finds mismatched complementary pieces of DNA, it can act as an exonuclease and remove DNA bases in a 3' to 5' direction until it reaches perfect matching again.

According to the present invention, small pieces of targeting DNA that are complementary to a specific region of the TH gene are placed in contact with a parental DNA strand during the DNA replication process. It is a general property of DNA that has been inserted into a cell to hybridize and therefore recombine with other DNA sequences through shared homologous regions. If this complementary strand is attached to an oligonucleotide that contains a mutation or a different sequence of DNA, it too is incorporated into the newly synthesized strand as a result of the recombination. As a result of the proofreading function of the polymerase, it is possible for the new sequence of DNA to serve as the template. Thus, the transfected DNA is incorporated into the genome.

An oligonucleotide that is complementary to a selected region of the TH gene can be synthesized or otherwise obtained, such as by appropriate restriction of the native DNA at specific recognition sites bounding the region of interest. This oligonucleotide will act as a targeting device upon insertion into the cell and will hybridize to its homologous region within the genome. If this hybridization occurs during DNA replication, this oligonucleotide, and any additional DNA sequence attached thereto, will act as an Okazaki fraoment and will be backstitched into the newly synthesized daughter strand of DNA.

As used according to the present invention, attached to these pieces of targeting DNA are regions of DNA that encode segments of TH containing sequences encoding the amino acid substitutions.

The recombinant DNA molecules useful for the methods of the present invention can be produced through any of a variety of means, such as, for example, DNA or RNA synthesis, or more preferably, by application of recombinant DNA techniques. Techniques for synthesizing such molecules are disclosed by, for example, Wu, R., et al. (*Prog. Nucl. Acid. Res. Molec. Biol.* 21:101-141 (1978)). Procedures for constructing recombinant molecules are disclosed in detail by Sambrook et al., supra.

Typically, the TH gene is cloned from a library of expression vectors which has been prepared by cloning DNA, either genomic or cDNA, preferably cDNA, from a cell capable of expressing the gene, into an expression vector. A preferred library is one derived from PC12, or, more preferably, from cells of human origin. The library is then screened for members capable of expressing the TH gene using an antibody specific for TH (either wild-type or variant). TH-encoding DNA is extracted and purified from a cell which is capable of expressing the TH gene. The purified DNA is fragmentized (by shearing, endonuclease digestion, etc.) to produce a pool of DNA fragments. DNA fragments from this pool are then cloned into an expression vector in order to produce a library of expression vectors whose members each contain a unique cloned DNA fragment. More preferably, a cDNA library is prepared from mRNA extracted from the TH-expressing cells, and cloned into an expression vector.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. An appropriate mammalian host cell would be any mammalian cell capable of expressing the cloned TH sequences. Procedures for preparing cDNA or genomic DNA libraries are disclosed by Sambrook et al., supra.

A DNA sequence encoding TH may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the TH gene sequence may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted. Two DNA sequences (such as a promoter region sequence and a coding sequence) are said to be operably linked if the nature of the linkage between the two DNA sequences does not (1) result in the introduction of a frame-shift mutation, (2) interfere with the ability of the promoter region sequence to direct the transcription of the coding sequence, or (3) interfere with the ability of the coding sequence to be transcribed by the promoter region sequence. A promoter region would be operably linked to a DNA sequence if the promoter were capable of effecting transcription of that DNA sequence. Thus, to express the protein, transcriptional and translational signals recognized by the host cell are necessary.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

The promoter sequences useful for the genetic constructs of the present invention may be either prokaryotic, eukaryotic or viral. Suitable promoters are repressible, or, more preferably, constitutive. Useful eukaryotic promoters include the promoter of the mouse metallothionein I gene (Hamer, D., et al., *J. Mol. Appl. Gen.* 1:273-288 (1982)); the TK promoter of Herpes virus (McKnight, S., *Cell* 31:355-365 (1982)); the SV40 early promoter (Benoist, C., et al., *Nature (London)* 290:304-310 (1981)). A preferred promoter for human fibroblasts, is the collagen promoter (Prockop, D. J. et al., *N. Eng. J. Med.* 301:13-23, 77-85 (1979); Eyre, D. R., *Science* 207:1315-1322 (1980); Martin, G. R. et al., *Trends Bioch. Sci.* 10:285-287 (1985)). A most preferred promoter is a cytomegalovirus (CMV) promoter, in combination with a bacteriophage T7 promoter.

The "polymerase chain reaction or "PCR" is an in vitro enzymatic method capable of specifically increasing the concentration of a desired nucleic acid molecule (Mullis, K. et al., *Cold Spring Harbor Symp. Quant. Biol.*

51:263-273 (1986); Erlich, H. et al., EP 50,424; EP 84,796, EP 258,017, EP 237,362; Mullis, K., EP 201,184; Mullis, K. et al., U.S. Pat. No. 4,683,202; Erlich, H., U.S. Pat. No. 4,582,788; and Saiki, R. et al.. U.S. Pat. No. 4,683,194). PCR provides a method for selectively increasing the concentration of a particular sequence even when that sequence has not been previously purified and is present only in a single copy in a sample. The method can be used to amplify either single- or double-stranded DNA. The method involves use of two oligonucleotide probes to serve as primers for the template-dependent, polymerase-mediated replication of a desired nucleic acid molecule.

The precise nature of the two oligonucleotide probes is critical to the success of the PCR method. As is well known, a molecule of DNA or RNA possesses directionality, which is conferred through the 5'-3' linkage of the phosphate groups. Sequences of DNA or RNA are linked together through the formation of a phosphodiester bond between the terminal 5' phosphate group of one sequence and the terminal 3' hydroxyl group of a second sequence. Polymerase-dependent amplification of a nucleic acid molecule proceeds by the addition of a 5' nucleotide triphosphate to the 3' hydroxyl end of a growing nucleic acid molecule. Thus, the action of a polymerase extends the 3' end of a nucleic acid molecule. These inherent properties are exploited in the selection of the oligonucleotide probes for PCR. The oligonucleotide probes of the PCR method are selected to contain sequences identical to, or complementary to, sequences which flank the particular nucleic acid sequence whose amplification is desired.

More specifically, the "first" probe must have a sequence that is capable of hybridizing to an oligonucleotide sequence located 3' to the desired sequence, whereas the "second" probe is designed to contain an oligonucleotide sequence identical to a sequence located 5' to the desired region. Both probes possess 3' hydroxy groups, and therefore can serve as primers for nucleic acid synthesis.

In the PCR, the reaction conditions are cycled between those conducive to hybridization and nucleic acid polymerization, and those which result in the denaturation of duplex molecules. In the first step, the sample nucleic acid is transiently heated, and then cooled, in order to denature any double-stranded molecules. The "first" and "second" probes are then added to the sample at a concentration greatly exceeding that of the desired nucleic acid molecule. When the sample is incubated under conditions conducive to hybridization and polymerization, the "first" probe will hybridize to the sample nucleic acid molecule at a position 3' to the sequence to be amplified. If the sample nucleic acid molecule was initially double-stranded, the "second" probe will hybridize to the complementary strand of the nucleic acid molecule at a position 3' to the sequence which is the complement of the sequence whose amplification is desired. Upon addition of a polymerase, the 3' ends of the "first" and (if the nucleic acid molecule was double-stranded) "second" probes will be extended. The extension of the "first" probe will result in the synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. Reviews of the PCR are provided by Mullis, K. B. (*Cold Spring Harbor Symp. Quant. Biol.* 51:263-273 (1986)); Saiki, R. K., et al. (*Bio/Technology* 3:1008-1012 (1985)); and Mullis, K. B., et al. (*Meth. Enzymol.* 155:335-350 (1987)).

The present invention is also directed to an antibody specific for an epitope of the variant TH of the present invention which distinguishes it from the wild-type TH. Such an antibody therefore has little or no cross-reactivity with wild-type TH.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules derived from the sera of animals immunized with an antigen.

Monoclonal antibodies are a substantially homogeneous population of antibodies to specific antigens. MAbs may be obtained by methods known to those skilled in the art. See, for example Kohler and Milstein, *Nature* 256:495-497 (1975) and U.S. Pat. No. 4,376,110. Such antibodies may be of any immunoglobulin class including IgG, IgM, IgE, IgA, IgD and any subclass thereof. The hybridoma producing the mAbs of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules different portions of which are derived from different animal species, such as a variable region derived from a murine mAb and a human immunoglobulin constant region. Chimeric antibodies and methods for their production are known in the art ( Cabilly et al, *Proc. Natl. Acad. Sci. USA* 81:3273-3277 (1984); Morrison et al.. *Proc. Natl. Acad. Sci. USA* 81:6851-6855 (1984); Boulianne et al., *Nature* 312:643-646 (1984); Neuberger et al., *Nature* 314:268-270 (1985); Taniguchi et al., European Patent Application 171496 (published Feb. 19, 1985); Liu et al.. *Proc. Natl. Acad. Sci. USA* 84:3439-3443 (1987); Better et al., *Science* 240:1041-1043 (1988)).

An anti-idiotypic (anti-Id) antibody is an antibody which recognizes unique determinants generally associated with the antigen-binding site of an antibody. An anti-Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316-325 (1983)).

Cells useful for the present invention, as hosts for the DNA encoding the variant TH, and as sources of the variant TH enzyme having higher activity than the wild-type, may be of neural, paraneural, or non-neural origin. The cells must be capable of incorporating the variant TH-encoding DNA of the present invention, and expressing the TH enzyme. Furthermore, the cells must be implantable in vivo, either alone or within a biocompatible polymer capsule, and must survive for sufficiently long in the animal host to provide the desired benefit, for example the provision of DA to a DA-deficient brain region.

By the term "neural or paraneural origin" is intended a cell which is derived from the embryonic neural crest. A preferred example of a cell of paraneural origin is a adrenal medullary chromaffin cell. The precursor cells to the mammalian adrenal medulla are of neural crest origin and possess the potential to develop along either neuronal or endocrine lines of differentiation (Bohn, M. C. et al., 1981, supra; Bohn, M. C. et al., *Devel. Biol.* 89:299-308 (1982); Unsicker, K., *Develop. Biol.* 108:259-268 (1985)). Chromaffin cells from the rat, monkey, and human adrenal medulla, when removed from adrenal cortical influences and exposed to nerve growth factor (NGF), change from an endocrine to a neuronal phenotype (Notter, M. F. et al., *Cell Tiss. Res.* 244:69-70 (1986); Stromberg, I. et al., *Exp. Brain Res.* 60:335-349 (1985); Unsicker, K. et al., 1978, supra). When co-grafted with cerebral cortical or hippocampal tissue into the anterior chamber of the rat eye, adrenal chromaffin cells form nerve fibers which innervate the adjacent co-grafted brain tissue (Olson, L. A. et al., *Exp. Neurol.* 70:14-426 (1980)). Another paraneural cell type is a retinal pigment epithelium cell (Song, M-K et al., *J. Cell. Physiol.* 148:196-203 (1990)).

Also useful for the present invention are established neural cell lines. Many neuronal clones which are electrically active with appropriate surface receptors, specific neurotransmitters, synapse forming properties and the ability to differentiate morphologically and biochemically into normal neurons, have been used as model systems of development. Neural lines may express a tremendous amount of genetic information which corresponds to the genetic expression seen in CNS neurons. Such cells are described in the following references: Kimhi, Y. et al., *Proc. Natl. Acad. Sci. USA* 73:462-466 (1976); Kimhi, Y. et al., In: *Excitable Cells in Tissue Culture*, Nelson, P. G. et al., eds., Plenum Press, New York, 1977, pp. 173-245; Prasad, K. M. et al., In: *Control of Proliferation of Animal Cells*. Clarkson, B. et al., eds., Cold Spring Harbor Laboratory Press, Cold Spring Harbor, N.Y., 1974, pp. 581-594; Puro, D. G. et al.. *Proc. Natl. Acad. Sci. USA* 73:3544-3548 (1976); Notter, M. F. et al., *Devel. Brain Res.* 26:59-68 (1986); Schubert, D. et al., *Proc. Natl. Acad. Sci. USA* 67:247-254 (1970); Kaplan, B. B. et al., In: *Basic and Clinical Aspects of Molecular Neurobiology*, Guffrida-Stella, A. M. et al., eds., Milano Fondozione International Manarini (1982).

A major advantage of these cultured cells has been the potential to manipulate the environment, as well as the cells themselves, in controlling the phenotype and genotype. These cells are preferably treated to render them morphologically and biochemically differentiated in vitro and must be rendered permanently amitotic before implantation, which further aids in their survival (Gupta, M. et al., *Dev. Brain Res.* 19:21-29 (1985)). Treatment of cells in vitro with NGF to stimulate neural cell differentiation followed by exposure to antimitotic agents to inhibit cell proliferation, does not deleteriously affect catecholamine neurotransmitter expression nor viability and is of value for stimulating performance following transplant.

Therefore, in one embodiment of the present invention, cell line cells, either before or after transfection with the genetic constructs of the present invention, are modulated in vitro with the appropriate growth or differentiation factor and with an amitotic agent before transplantation in order to promote cell survival and prevent expression of the malignant potential.

Another important source of potential graft material are cells engineered by somatic cell hybridization. Hybrid cells can be formed which retain the properties of differentiated cells. For examples, hybrids derived from fusion of sympathetic ganglia and neuroblastoma cells can synthesize DA (Greene, L. A. et al., *Proc. Natl. Acad. Sci. USA* 82:4923-4927 (1975)). Embryonic precursors to dopaminergic neurons from the CNS can be fused with mitotic cells to incorporate both genomes into a single one that loses extra chromosomes over time and results in a new hybrid line. It is within the skill of the art to produce such hybrid neural or paraneural cells without undue experimentation, screen them for the desired traits, and select those having the best potential for transfection and transplantation.

Another useful source of cells for transplantation according to the present invention is the adrenal medulla. This neural crest-derived tissue has been involved in clinical trials (see Background) to treat PD. Adult monkey adrenal medulla can be cultured in vitro for at least about three weeks as single cells (Notter, M. F. et al., *Cell Tiss. Res.* 244:69-76 (1986)). These cells respond to NGF by phenotypic alteration from the epithelioid, glandular morphology, to a neuronal morphology in which cells show extensive neuritic arborizations containing microtubular arrays. This neuronal phenotype appears to be critical for long term survival of rat medullary cells in host CNS as well as their integration with host tissue (Stromberg, L. et al., supra). Transplanted adrenal medulla tissue can correct functional deficits resulting from nigrostriatal DA depletion in rats (see, for example, Freed et al., 1981, supra). This is thought to be brought about by diffusion of DA from the transplant, a phenomenon that decreases three to six months after transplantation. Cells transfected with the variant TH genetic constructs according to the present invention are expected to have enhanced DA-producing capacity over time. Furthermore, NGF treatment of the transplanted cells induces fiber outgrowth from the transplant into the host, thus inducing a longer lasting therapeutic effect.

Retinal pigment epithelial cells can secrete DA and may also be used for transfection and implantation according to the present invention (Li, L. et al., *Exp. Eye Res.* 47:771-785 (1988); Lui, G. M. et al.. *Proc. Int'l. Soc. Eye Res.* 6:172 (1990); Li, L. et al., *Inv. Ophthal. Vis. Sci.* 31(Suppl):595 (1990, abstr. 2915-13); Sheedlo, H. J. et al., ibid., abstr. 2916-14; Fektorovich, E. G. et al., ibid. (abstr. 2917-15); Song, M-K et al., supra).

An additional embodiment of the present invention is directed to transplantation of cells combined with the treatment, either in vitro prior to transplant, in vivo after transplant, or both, with the appropriate growth-/differentiation factor.

In a preferred embodiment of the present invention, cells which are not of neural or paraneural origin, but which have been altered to produce a substance of neurological interest, are used. A preferred cell type is a human fibroblast, such as a foreskin fibroblast, which is easily obtained and cultured. For use in the present invention, the cells are transfected with the DNA encoding a TH variant of the present invention, of rat or, preferably, of human origin, as described herein, to express TH having increased enzymatic activity. For examples of cells which can be transfected to express proteins of neurological interest, see: Gage, F. H. et al., *Neuroscience* 23:795-807 (1987); Rosenberg, M. B. et al., *Science* 242:1575-1578 (1988); Shimohama, S. et al., *Mol. Brain Res.* 5:271-278 (1989); which are hereby incorporated by reference.

The cells useful in the methods of the present invention may be xenogeneic (=heterologous, i.e., derived from a species different from the recipient), allogeneic (=homologous, i.e., derived from a genetically different member of the same species as the recipient) or autologous, wherein the recipient also serves as the donor. Preferred cells for human recipients are of human origin, either autologous or allogeneic.

The number of cells needed to achieve the purposes of the present invention is variable depending on the size, age and weight of the subject, the nature of the underlying disease, other concurrent therapies, and the like. This can be determined by one of skill in the art without undue experimentation. In an adult human, an effective number of cells expressing the variant TH are in the range of about $1 \times 10^3$ to about $1 \times 10^7$ cells, more preferably about $5 \times 10^3$ to about $1 \times 10^6$ cells.

Cells useful for the present invention may be transiently or stably transfected, by methods well-known in the art, depending on the use of the cells. For implantation into the brain of humans, stably transfected cells are preferred. Stable transfection of At20 cells by rat TH variants is exemplified below. It is within the skill of the art to stably or transiently transfect mammalian cells, of human or non-human origin, with the DNA constructs of the present invention.

The cells may be implanted in a recipient's brain directly or encapsulated in a selectively permeable biocompatible polymer capsule which allows release of the products of these cells, for example, DA, yet protects the cells from attack by antibodies or host cells (See, for example, Aebischer, P. et al., *Brain Res.* 448:364-368 (1988); Winn, S. R. et al.. *J. Biomed Mater Res.* 23:31-44 (1989)). For example, the polymer capsules may consist of polyvinyl chloride acrylic copolymer XM-50. Such permselective material can completely prevent the invasion of the encapsulated tissue by host cells, and presumably antibodies and viruses as well, based on the permeability of the membrane. When DA-releasing polymer rods were encapsulated into such a permselective polymer and implanted into denervated rat striatum, alleviation of the experimental induced Parkinson disease symptoms was achieved (Winn S. R. et al., *Exp. Neurol.* 105:244-50 (1989). U.S. Pat. No. 4,892,538 (Aebischer et al., issued Jan. 9, 1990) discloses a cell culture device for implantation in a subject for delivery of a neurotransmitter comprising secreting cells within a semipermeable membrane which permits diffusion of the neurotransmitter while excluding viruses, antibodies and other detrimental agents present in the external environment. The semipermeable membrane is of an acrylic copolymer, polyvinylidene fluoride, polyurethane, polyalginate, cellulose acetal, polysulphone, polyvinyl alcohol, polyacrylonitrile, or their derivatives or mixtures and permits diffusion of solute of up to 50 kD molecular weight. The device may be made retrievable so that the contents may be renewed or supplemented, and the cells are protected against immunological response and viral infection.

The methods of the present invention are intended for use with any mammal which may experience the beneficial effects of the methods of the invention. Foremost among such mammals are humans, although the invention is not intended to be so limited, and is also applicable to veterinary uses.

Having now generally described the invention, the same will be more readily understood through reference to the following examples which are provided by way of illustration, and are not intended to be limiting of the present invention, unless specified.

EXAMPLE I

Plasmid Constructs Usino PCR

A 1.8 kb rat TH cDNA fragment (1788 bp), including 1494 bp TH-coding region, an 11 bp 5'-flanking end, a 284 bp 3'-flanking end and a 12 bp linker-site, was generated from a PC12 cDNA library and amplified by PCR.

The cDNA reaction mixture was subjected to 40 cycles of PCR (Cetus-Perkin Elmer). The conditions used for PCR were: 1 min at 94° C; annealing at 37° C. for 2 min; and 3 min primer extension reaction at 72° C.

The TH-PGem vector was constructed by inserting the 1.8 kb XhoI fragment, which was isolated following amplification by PCR, into the XhoI site of the plasmid pSP72 (Promega) to give the construct pSP72-TH. A 1.8 kb fragment obtained by XhoI digestion of the pSP72-TH construct was subcloned into the XhoI site of the CDM8 vector (Seed, B., *Nature* 329:840-842 (1987)).

EXAMPLE II

Site-Directed Mutagenesis

Figure 2:
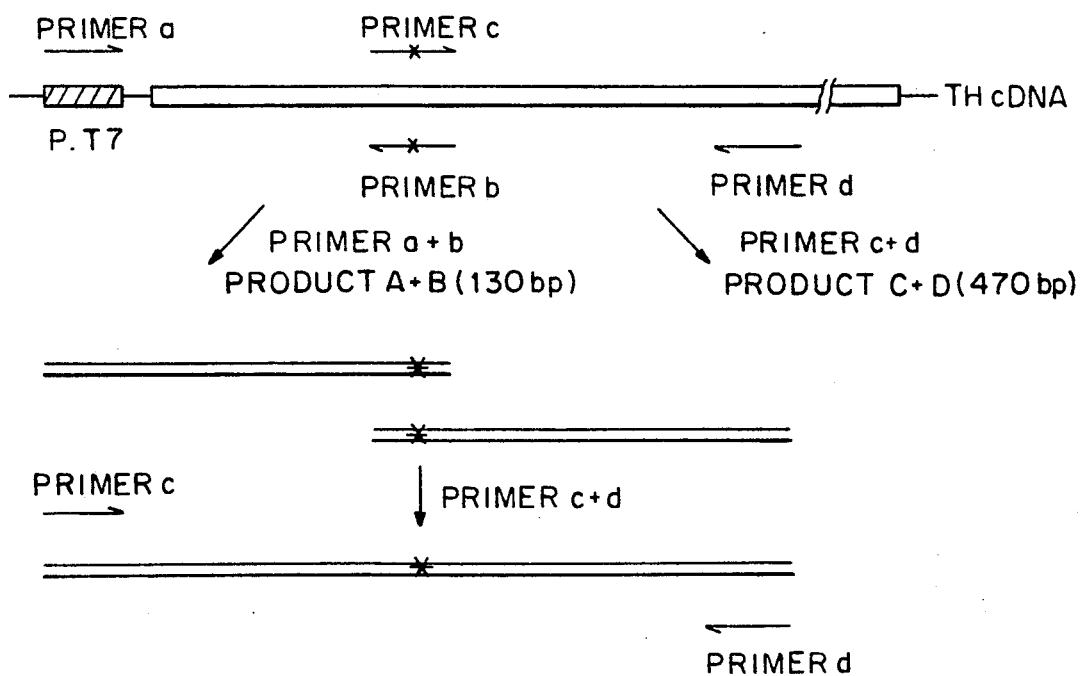
FIG. 2 provides a schematic diagram of the steps used in performing site-directed mutagenesis of the phosphorylation site (Ser-40) in rat TH. PCR was used to mutate TH at the Ser-40 position. The open box represents rat TH cDNA. The solid box represents the T7 promoter in the expression vector. Horizonal arrows indicate the position and direction of DNA synthesis primed by an appropriate oligonucleotide. Products AB and CD are amplified from TH cDNA using primer a+b and primer c+d, respectively. The top strand of AB and bottom strand of CD overlap by the same modified ends and act as primers. The strands are extended and amplified with primers a+d.

Mutant rat cDNA molecules having substitute amino acids for Ser at positions 8, 19, 31, 40 and 153, or having a substitute at the consensus sequence adjacent to the Ser residues, were constructed by site-directed in vitro mutagenesis using the procedure of Horton et al. (Horton, R. M. et al.. *Biotechniques* 8:528-535 (1990)). The synthetic mutagenic primers used for mutant construction appear in Table 1 (above). Outside primer "a" (see FIG. 2) was a 17-mer having the same sequence as the T7 promoter. Outside primer "d" (see FIG. 2) was a 20-mer having a sequence complementary to the first strand of TH DNA corresponding to bases 592-612. The procedure is schematically illustrated in FIGS. 1 and 2.

The PCR products were isolated using gel electrophoresis, digested with HindIII/PstI, and replaced in the HindIII/PstI site of thr cDM8TH expression vector using T4 DNA polymerase. The DNA sequence of all of the mutants was obtained to confirm the presence of the appropriate mutations.

TH cDNA sequence was determined from the double-strand template using the GemSeq K/RT TM system and the chain-termination method (Chen, E. Y. et al., *DNA* 4:165-170 (1985)).

Figures 3, 4:
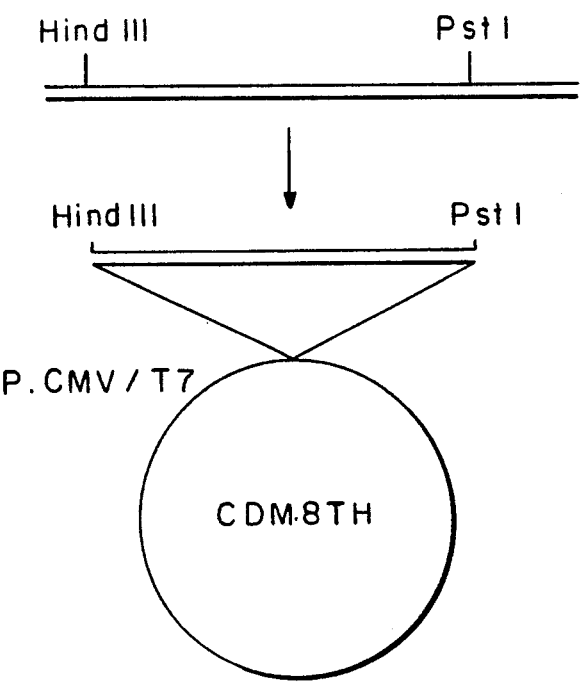
FIG. 3 describes the construction of the Ser-40 mutant in a eukaryotic expression vector. PCR products are digested by HindIII and PstI. The HindIII/PstI region of CDM8TH is replaced by a 170bp DNA fragment containing Ser-40 point mutation (using T4 ligase).
FIG. 4 shows the nucleotide sequence of mutant (M) and wild-type (WT) sense DNA strands obtained by double stranded DNA sequencing. Altered bases are boxed.

The variant sequences are shown in FIG. 4.

EXAMPLE III

Transfection with TH cDNA and TH Enzyme Activity

AtT-20 cells were grown in MEM medium supplemented with 5% fetal calf serum. When the cells reached 60% confluence, 20 μg of wild-type or variant TH DNA was co-transfected with DNA of the plasmid pSVNeo containing the neomycin-resistance gene, using the calcium phosphate precipitation method (Wigler, M. I. et al., *Cell* 16:777-785 (1979)). Transfected cells were selected in medium containing 600 μg/ml G418. Cell colonies with high TH activity were selected. The cells were homogenized in 50 mM Na acetate buffer, pH 6.1. TH activity was measured using a radioenzymatic procedure well-known in the art.

TH activity was undetectable in untransfected cells. The TH enzymatic activity in the transfected cells was found to be as follows. The wild-type had activity of 1500 pmol of product/hr/mg. Three variants with substitutions of Ser-40 were examined The Tyr-containing variant (Tyr$^{m40}$) had an activity of 4500 pmol/hr/mg. The Leu$^{m40}$ variant had activity of 4800 pmol/hr/mg. The Cys$^{m40}$ had activity of 1400 pmol/hr/mg. Therefore, substitution of Tyr or Leu at this site caused a three-fold or greater enhancement of TH enzyme activity.

Western blot analysis of TH revealed the following. Extracts of transfected, but not of untransfected, cells showed an immunoreactive band with an apparent MW of 60 kDa, which was identical to that of rat striatal TH.

The references cited above are all inoorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A variant tyrosine hydroxylase protein moelcule having at least one amino acid substitution in the N-terminal fifty-five amino acid residues of the wild-type protein sequence, said at least one substitution corresponding to an amino acid selected from Ser-8, Ser-31, Arg-37, Arg-38, Gln-39, Ser-40, Leu-41, Ile-42, Glu-43, Asp-44, Ala-45, Arg-46 or Lys-47 of a rat or human tyrosine hydroxylase, wherein the tyrosine hydroxylase enzymatic activity of said variant protein is at least three fold greater than the enzymatic activity of the wild-type protein, and wehrein said substitution is a larger amino acid for a smaller amino acid, a smaller amino acid for a larger amino acid, or a hydrophilic amino acid for a hydrophobic amino acid or a hydrophobic amino aicd for a hydrophilic amino acid.

2. A protein according to claim 1 wherein said substitution is Ser-40 to Tyr or Ser-40 to Leu.

3. A variant tyrosine hydroxylase protein according to claim 1, wherein the substitution is at one of said Ser residues of the wild type protein and the amino acid substituted therefore is selected from Try, Trp, Leu, Ile, Val or Phe.

4. A variant tyrosine hydroxylase protein according to claim 1, wherein the substitution is at one of said Ser residues of the wild type protein and the amino acid substituted therefore is selected from Tyr or Leu.

5. A variant tyrosine hydroxylase protein according to claim 1, wherein the substitution is at one of said said Leu or Ile residues of the wild type protein and the amino acid substituted therefore is selected from Gly, Met or Cys.

* * * * *